United States Patent
Busch-Petersen et al.

(10) Patent No.: US 7,579,345 B2
(45) Date of Patent: Aug. 25, 2009

(54) MUSCARINIC ACETYLCHOLINE RECEPTOR ANTAGONISTS

(75) Inventors: Jakob Busch-Petersen, King of Prussia, PA (US); Christopher E. Neipp, King of Prussia, PA (US); Michael R. Palovich, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 364 days.

(21) Appl. No.: 11/568,909

(22) PCT Filed: May 26, 2005

(86) PCT No.: PCT/US2005/018563

§ 371 (c)(1), (2), (4) Date: Nov. 10, 2006

(87) PCT Pub. No.: WO2005/118594

PCT Pub. Date: Dec. 15, 2005

(65) Prior Publication Data

US 2007/0232599 A1    Oct. 4, 2007

Related U.S. Application Data

(60) Provisional application No. 60/575,329, filed on May 28, 2004.

(51) Int. Cl.
C07D 498/08 (2006.01)
A61K 31/537 (2006.01)
(52) U.S. Cl. ................................... 514/230.5; 544/105
(58) Field of Classification Search ................ 544/105; 514/230.5

See application file for complete search history.

(56) References Cited

U.S. PATENT DOCUMENTS 6,476,046 B1    11/2002   Wu et al.

Primary Examiner—Kahsay T Habte
(74) Attorney, Agent, or Firm—Dara L. Dinner; Charles M. Kinzig

(57) ABSTRACT

Muscarinic Acetylcholine Receptor Antagonists and methods of using them are provided.

21 Claims, No Drawings

MUSCARINIC ACETYLCHOLINE RECEPTOR ANTAGONISTS

This application is a 35 U.S.C. 371 application, which claims the benefit of U.S. Provisional Application No. 60/575,329, filed 28-May-2004.

FIELD OF THE INVENTION

This invention relates to tertiary alcohol derivatives of 8-azoniabicyclo [3.2.1]octanes, their pharmaceutical compositions, and uses thereof in treating muscarinic acetylcholine receptor mediated diseases of the respiratory tract.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs where they mediate many of the vital functions. Muscarinic receptors can mediate both inhibitory and excitatory actions. For example, in smooth muscle found in the airways, $M_3$ mAChRs mediate contractile responses. For review, please see Caulfield (1993 *Pharmac. Ther.* 58:319-79), incorporated herein by reference.

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 *Am J Respir Crit Care Med* 158(5, pt 3) S 154-60).

Three subtypes of mAChRs have been identified as important in the lungs, $M_1$, $M_2$ and $M_3$ mAChRs. The $M_3$ mAChRs, located on airway smooth muscle, mediate muscle contraction. Stimulation of $M_3$ mAChRs activates the enzyme phospholipase C via binding of the stimulatory G protein Gq/11 (Gs), leading to liberation of phosphatidyl inositol-4,5-bisphosphate, resulting in phosphorylation of contractile proteins. $M_3$ mAChRs are also found on pulmonary submucosal glands. Stimulation of this population of $M_3$ mAChRs results in mucus secretion.

$M_2$ mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal $M_2$ mAChRs are located on postganglionic parasympathetic nerves. Under normal physiologic conditions, neuronal $M_2$ mAChRs provide tight control of acetylcholine release from parasympathetic nerves. Inhibitory $M_2$ mAChRs have also been demonstrated on sympathetic nerves in the lungs of some species. These receptors inhibit release of noradrenaline, thus decreasing sympathetic input to the lungs.

$M_1$ mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation (Fryer et al. 1999 *Life Sci* 64 (6-7) 449-55). This mAChR dysfunction results in airway hyperreactivity and hyperresponsiveness mediated by increased stimulation of $M_3$ mAChRs. Thus the identification of potent mAChR antagonists would be useful as therapeutics in these mAChR-mediated disease states.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 *Am. J Respir. Crit. Care Med.* 163:1256-1276).

Despite the large body of evidence supporting the use of anti-cholinergic therapy for the treatment of airway hyperreactive diseases, relatively few anti-cholinergic compounds are available for use in the clinic for pulmonary indications. More specifically, in United States, Ipratropium Bromide (Atrovent©; and Combivent©, in combination with albuterol) is currently the only inhaled anti-cholinergic marketed for the treatment of airway hyperreactive diseases. While this compound is a potent anti-muscarinic agent, it is short acting, and thus must be administered as many as four times daily in order to provide relief for the COPD patient. In Europe and Asia, the long-acting anti-cholinergic Tiotropium Bromide (Spiriva©) was recently approved, however this product is currently not available in the United States. Thus, there remains a need for novel compounds that are capable of causing blockade at mAChRs which are long acting and can be administered once-daily for the treatment of airway hyperreactive diseases such as asthma and COPD.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anti-cholinergic use.

SUMMARY OF THE INVENTION

This invention provides for a method of treating a muscarinic acetylcholine receptor (mAChR) mediated disease, wherein acetylcholine binds to an mAChR and which method comprises administering an effective amount of a compound of formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

The present invention also provides for the novel compounds of Formula (I), and pharmaceutical compositions comprising a compound of Formula (I), and a pharmaceutical carrier or diluent.

The compounds according to this invention have the structure shown by Formula (I):

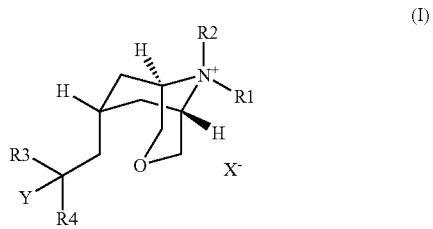

wherein
the side chain indicated may have either endo or exo orientation but is preferred with endo, R1 and R2 are, independently, selected from the group consisting of: a bond, hydrogen, $(C_1-C_{12})$alkyl, $(C_2-C_{10})$alkenyl, $(C_1-C_6)$alkyl$(C_3-C_6)$cycloalkyl, $(C_1-C_{10})$alkyl-aryl, $(C_1-C_{10})$alkyl-OH, $(C_1-C_6)$alkyl-CN, $(C_1-C_{10})$ alkyl-halogen,$(C_1-C_6)$alkyl-CF$_3$, $(C_1-C_6)$alkyl-alkoxy, and $(C_1-C_6)$alkyl-O—$(C_1-C_6)$alkyl-OCH$_3$, R3 and R4 are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, aryl, optionally substituted aryl, heteroaryl having 5 to 6 carbon atoms and N or O as the heteroatom, optionally substituted heteroaryl having 5 to 6 carbon atoms and N or O as the heteroatom, heterocycloalkyl having 5 to 6 carbon atoms and N or O as the heteroatom, and heterocycloalkyl-alkyl having 6 to 10 carbon atoms and N or O as the heteroatom, Y is hydroxy (—OH) or cyano (—CN); and X$^-$ is a physiologically acceptable anion associated with the positive charge of the N atom. X$^-$ may be but is not limited to chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

Illustrative examples of this invention include:
2-[(7-Endo)-9-methyl-3-oxa-9-azabicyclo[3.3.1]non-7-yl]-1,1-di-2-thienylethanol;
3-[(7-Endo)-9-methyl-3-oxa-9-azabicyclo[3.3.1]non-7-yl]-2,2-di-2-thienylpropanenitrile;
2-[(7-Endo)-9-methyl-3-oxa-9-azabicyclo[3.3.1]non-7-yl]-1,1-diphenylethanol;
2-[(7-Exo)-9-methyl-3-oxa-9-azabicyclo[3.3.1]non-7-yl]-1,1-di-2-thienylethanol;
(7-Endo)-7-(2-hydroxy-2,2-di-2-thienylethyl)-9,9-dimethyl-3-oxa-9-azoniabicyclo[3.3.1]nonane iodide;
(7-Endo)-7-(2-cyano-2,2-di-2-thienylethyl)-9,9-dimethyl-3-oxa-9-azoniabicyclo[3.3.1]nonane bromide;
(7-Endo)-7-(2-cyano-2,2-diphenylethyl)-9,9-dimethyl-3-oxa-9-azoniabicyclo[3.3.1]nonane iodide; and
(7-Exo)-7-(2-hydroxy-2,2-di-2-thienylethyl)-9,9-dimethyl-3-oxa-9-azoniabicyclo[3.3.1]nonane bromide.

METHODS OF PREPARATION

The compounds of Formula (I) may be obtained by applying synthetic procedures, some of which are illustrated in the Schemes below. The synthesis provided for these Schemes is applicable for producing compounds of Formula (I) having a variety of different R$_X$ groups (X=1,2) which are reacted, employing substituents which are suitably protected, to achieve compatibility with the reactions outlined herein. Subsequent deprotection, in those cases, then affords compounds of the nature generally disclosed. While the Schemes are shown with compounds only of Formula (I), this is merely for illustration purposes only.

Scheme 1

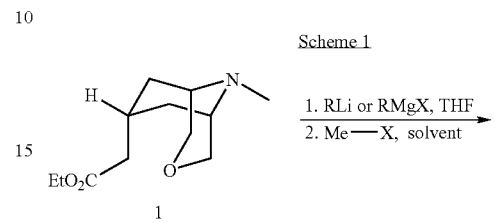

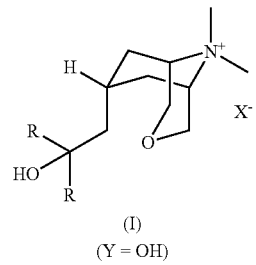

As outlined in Scheme 1, the desired compounds of Formula (I) (Y=OH) can be prepared via the reaction of the ester 1 with an excess of organolithium or Grignard reagent. Reaction of the tertiary nitrogen with either methyl iodide or methyl bromide gives the compound of Formula (I).

The required [3.3.1] bicyclic ester 1 can be prepared by the sequence of reactions shown in Scheme 2 starting from the ketone 2. The preparation of 2 and related compounds has been reported by Zirkle (Zirkle, C. L.; et al *J. Org. Chem.* 1961, 26, 395-407). In the event, the Homer-Emmons reaction of 2 using diethyl (cyanomethyl)phosphonate and sodium hydride provided the alkene 3. Hydrogenation of alkene 3 produced the nitrile 4. Subsequent hydrolysis and in situ esterification of 4 gave the ester 1.

Scheme 2

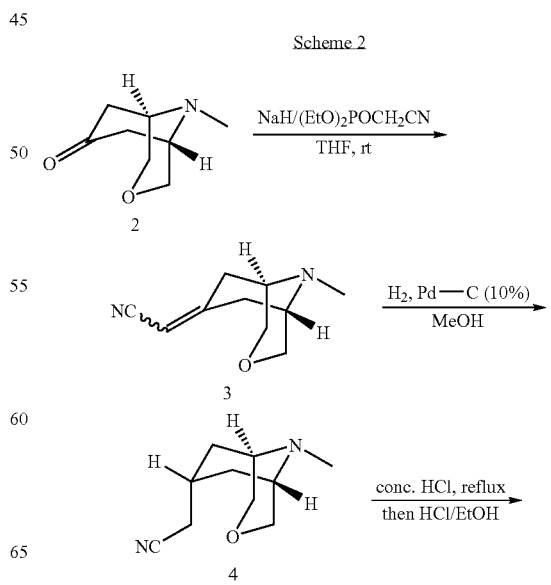

-continued

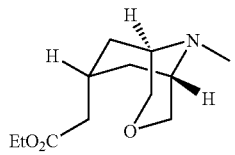

Alternatively, the exo isomer of ester 1 can also be prepared as outlined in Scheme 3. Specifically, a dissolving metal reduction of the alkene 3 with magnesium in MeOH provides the exo orientation of the side chain. The nitrile 5 is then hydrolyzed and esterified as shown to give the exo ester 6. Following a reaction sequence similar to that shown in Scheme 1, the ester 6 is then further elaborated to provide the compounds of Formula (I) with an exo side chain.

Scheme 3

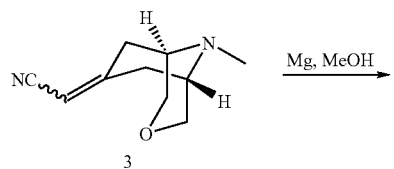

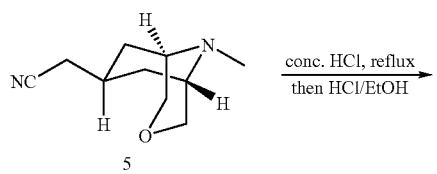

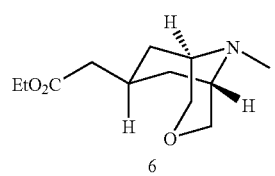

The tertiary alcohols shown in Scheme 1 may be transformed into a tertiary nitrile via a one-pot procedure. Specifically, sequential treatment of the tertiary amine 7 with AlCl$_3$ and then trimethylsilyl cyanide (TMSCN) gives the nitrile 8. Reaction of 8 with methyl bromide then provides the quaternary amine salt 9.

Scheme 4

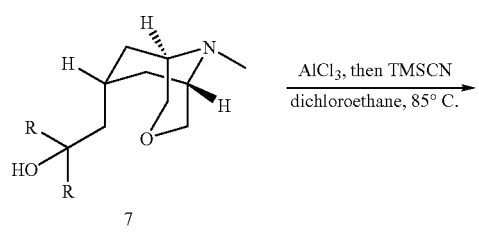

-continued

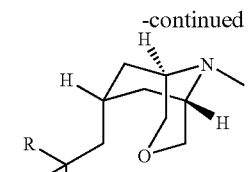

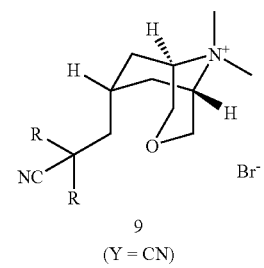

SYNTHETIC EXAMPLES

The invention will now be described by reference to the following Examples that are merely illustrative and are not to be construed as a limitation of the scope of the present invention. Unless otherwise indicated, all starting materials were obtained from commercial suppliers and used without further purification. All temperatures are given in ° C. Anhydrous solvents were purchased from Aldrich. Thin layer chromatography (t.l.c.) was carried out on silica. Flash chromatography was conducted according to the Still protocol (Still, W. C.; et al *J. Org. Chem.* 1978, 43, 2923-2925) using EMD (Merck) 9385 40-63d silica gel (230-400 mesh) with the indicated solvents unless stated otherwise. All $^1$H NMR spectra were taken on a 400 MHz instrument. Analytical LC/MS was conducted under the following conditions:

| Liquid Chromatograph System: | Shimadzu LC system with SCL-10A Controller and dual UV detector |
|---|---|
| Autosampler: | Leap CTC with a Valco six port injector |
| Column: | 1 mm × 40 mm, Aquasil (C18) |
| Flow Rate: | 0.3 mL/min |
| Injection Volume: | 2 μl |
| Temp: | room temperature |
| Solvents: | A: 0.02% Trifluoroacetic Acid/Water. B: 0.018% Trifluoroacetic Acid/Acetonitrile. |

| Gradient (Linear): | | | |
|---|---|---|---|
| Time (min) | Duration (min) | A% | B% |
| 0.00 | 0.00 | 95 | 5 |
| 0.00 | 0.01 | 95 | 5 |
| 0.01 | 3.20 | 10 | 90 |
| 3.21 | 1.00 | 10 | 90 |
| 4.21 | 0.01 | 95 | 5 |
| 4.31 | 0.40 | 95 | 5 |

(±)-(9-Methyl-3-oxa-9-azabicyclo[3.3.1]non-7-ylidene)ethanenitrile (3)

Diethyl (cyanomethyl)phosphonate (2.08 mL, 12.9 mmol) was added dropwise over 2.33 min to a stirred slurry of 95%

NaH (325 mg, 12.9 mmol) in anhydrous THF (24 mL) under argon at room temperature. After stirring for 40 min, a solution of 2 (1 g, 6.44 mmol) in THF (8 mL) was added in one portion. Stirring was continued for 22 h, whereupon MeOH (2 mL) was added in one portion. The mixture was concentrated under reduced pressure, and a 1 M solution of HCl (10 mL) was added. The mixture was extracted with EtOAc (2×5 mL), and the combined organic layers were washed with saturated $K_2CO_3$ (1×3 mL). These organic layers contained 3, as determined by TLC. The acidic aqueous layer was made basic with 6 M NaOH (2.5 mL) and extracted with EtOAc (4×5 mL). All organic layers were combined, dried ($Na_2SO_4$) and concentrated under reduced pressure. $^1H$ NMR ($CDCl_3$) of 3 showed some contaminants, but the material was of suitable purity to carry on for the next step in the reaction sequence.

LC/MS ESI $R_T$ 0.26 min $MH^+$ 179.2

[(7-Endo)-9-methyl-3-oxa-9-azabicyclo[3.3.1]non-7-yl]acetonitrile (4)

MeOH (4 mL) was added to a mixture of 3 (300 mg, 1.68 mmol) and 10% Pd-C (18 mg, 0.0168 mmol) under argon, and the flask was purged for 15 min with a $H_2$ balloon (note: to ensure efficient purging, the $H_2$ was introduced to the reaction flask via a 4 inch needle, where the needle tip was situated just above the reaction mixture). The reaction was stirred at room temperature for 2 d, and the reaction mixture was filtered through a pad of Celite 521. The filter cake was rinsed with MeOH (4×5 mL), and the combined filtrate was concentrated under reduced pressure. The residue was combined with another portion of 10% Pd-C (18 mg, 0.0168 mmol) under argon, and MeOH (4 mL) was added. The reaction flask was purged with $H_2$ as described above, and the reaction was stirred at room temperature for 30 h. The reaction was again filtered as above, and the reaction was run once more with 10% Pd-C (89 mg, 0.084 mmol) under $H_2$ for 18 h. The reaction mixture was filtered as shown above, and the combined filtrate was concentrated under reduced pressure and dried under high vacuum to give 265 mg (87%) of 4. $^1H$ NMR ($CDCl_3$) of 4 showed some contaminants, but the material was of suitable purity to carry on for the next step in the reaction sequence.

Ethyl [(7-endo)-9-methyl-3-oxa-9-azabicyclo[3.3.1]non-7-yl]acetate (1)

A solution of 4 (265 mg, 1.47 mmol) in concentrated HCl (3 mL) was heated at reflux with stirring for 2 h. EtOH (10 mL) was added, and stirring continued for 12 h. The reaction was concentrated under reduced pressure, and NaOH (1.6 g) and $H_2O$ (2 mL) were added. The mixture was stirred until the NaOH had dissolved, and the mixture was extracted with EtOAc (1×5 mL). According to LC/MS, this organic layer contained only the intermediate carboxylic acid and none of 1. The aqueous layer was made acidic with concentrated HCl (2 mL), combined with the organic layer, and concentrated under reduced pressure. The residue was taken up in a 2 M solution of HCl/EtOH (5 mL) and stirred at room temperature for 4 d. The reaction was concentrated under reduced pressure, and a mixture of saturated $K_2CO_3$ (3 mL) and EtOAc (5 mL) was added. The solids were filtered off and the filter cake was rinsed with EtOAc (4×5 mL). The combined filtrate was washed with saturated NaCl (1×2 mL), dried ($Na_2SO_4$), and concentrated under reduced pressure to give 174 mg (52%) of 1. The purity of 1 as determined by $^1H$ NMR ($CDCl_3$) was considered to be sufficient to carry on for the next step in the reaction sequence.

LC/MS ESI $R_T$ 1.20 min $MH^+$ 228.2

[(7-Exo)-9-methyl-3-oxa-9-azabicyclo[3.3.1]non-7-yl]acetonitrile (5)

Mg(0) (1.09 g, 44.9 mmol) was added to a solution of 3 (200 mg, 11.35 mmol) in MeOH (11 mL) under argon. The reaction was cooled to 0° C. (bath temp) and was allowed to warm slowly to room temperature. After 15 h, MeOH (10 mL) was added, followed by portionwise addition of concentrated HCl (10 mL) was added portionwise (exotherm). The reaction was stirred at room temperature until all solids had dissolved. The MeOH was removed under reduced pressure, and Celite 521 (8 g) was added. Added NaOH (6 g) and stirred the mixture until the NaOH had dissolved. EtOAc (20 mL) was added, and the solids were filtered off. The filter cake was rinsed with EtOAc (4×15 mL), and the combined filtrate was washed with saturated NaCl (2×5 mL). The organic layer was dried ($Na_2SO_4$) and concentrated under reduced pressure. The crude product (100 mg) was purified by flash chromatography on neutral alumina (20 g; Aldrich, 60 Å) eluting with 0.5% MeOH/EtOAc to give 32 mg (16%) of 5.

LC/MS ESI $R_T$ 0.85 min $MH^+$ 181.0

Ethyl [(7-exo)-9-methyl-3-oxa-9-azabicyclo[3.3.1]non-7-yl]acetate (6)

A solution of 5 (32 mg, 0.178 mmol) in concentrated HCl (1 mL) was heated at reflux with stirring for 2 h. EtOH (3 mL) was then added, and stirring continued at room temperature for 12 h. The EtOH was removed under reduced pressure, and NaOH (0.8 g) and $H_2O$ (2 mL) were added. The mixture was stirred until the NaOH had dissolved, and the aqueous layer was extracted with EtOAc (1×5 mL). According to LC/MS, this organic layer contained only the intermediate carboxylic acid and none of 6. The aqueous layer was made acidic with concentrated HCl (2 mL), combined with the organic layer, and concentrated under reduced pressure. The residue was taken up in a 2 M solution of HCl/EtOH (5 mL) and stirred at room temperature for 4 d. The reaction was concentrated under reduced pressure, and a mixture of saturated $K_2CO_3$ (3 mL) and EtOAc (5 mL) was added. The solids were filtered off and the filter cake was rinsed with EtOAc (4×5 mL). The combined filtrate was washed with saturated NaCl (1×2 mL), dried ($Na_2SO_4$), and concentrated under reduced pressure to give 34 mg (84%) of 6. The purity of 6 as determined by $^1H$ NMR ($CDCl_3$) was considered to be sufficient to carry on for the next step in the reaction sequence.

LC/MS ESI $R_T$ 0.87 min $MH^+$ 228.0

Example 1

2-[(7-Endo)-9-methyl-3-oxa-9-azabicyclo [3.3.1]non-7-yl]-1,1-di-2-thienylethanol A solution of 1 (167 mg, 0.735 mmol) was added dropwise as a solution in THF (1.8 mL) with stirring to a 1 M solution of 2-thienyllithium in THF (2.9 mL, 2.9 mmol) at −30° C. (bath temp) under argon. The reaction was stirred at room temperature for 5 h, whereupon $H_2O$ (3 mL) was added. The layers were separated, and the aqueous layer was extracted with EtOAc (3×2 mL). The combined organic layers were washed with saturated NaCl (1×1 mL), dried ($Na_2SO_4$), and concentrated under reduced pressure. The crude product was purified by flash chromatography on silica gel (20 g) eluting with 5% MeOH/$CH_2Cl_2$ (600 mL), followed by 10% MeOH/$CH_2Cl_2$ (300 mL) to give 174 mg (68%) of Example 1.

LC/MS ESI $R_T$ 1.28 min $MH^+$ 350.0

Example 2

3-[(7-Endo)-9-methyl-3-oxa-9-azabicyclo[3.3.1]non-7-yl]-2,2-di-2-thienylpropanenitrile AlCl$_3$ (237 mg, 1.79 mmol) was added to a slurry of Example 1 (125 mg, 0.358 mmol) in dichloroethane (7.2 mL) in a 2 dram vial. The vial was sealed with a Teflon-lined screwcap and the reaction was stirred at room temperature for 10 min. TMSCN (0.24 mL, 1.79 mmol) was then added, the vial was resealed, and the reaction was stirred at 85° C. (bath temp) for 20 h. The reaction was stirred at room temperature for 10 min, and a further portion of AlCl$_3$ (237 mg, 1.79 mmol) was added. Stirring continued for 10 min, whereupon another portion of TMSCN (0.24 mL, 1.79 mmol) was added. The reaction was stirred at 85° C. for 40 h, and the reaction was poured into a 2.5:1 mixture of saturated K$_2$CO$_3$/EtOAc (35 mL) with stirring. The black precipitate was filtered off, and the filter cake was rinsed with EtOAc (3×5 mL). The layers of the filtrate were separated, and the aqueous layer was extracted with EtOAc (3×5 mL). The combined organic layers were dried (Na$_2$SO$_4$) and concentrated under reduced pressure. The crude product was by flash chromatography on silica gel (8 g) eluting with 2% MeOH/CH$_2$Cl$_2$ (150 mL), followed by 5% MeOH/CH$_2$Cl$_2$ (100 mL) to give 49 mg (38%) of Example 2.

LC/MS ESI R$_T$ 1.72 min MH$^+$ 359.2

Example 3

2-[(3-Endo)-9-methyl-3-oxa-9-azabicyclo[3.3.1]non-7-yl]-1,1-diphenylethanol

Compoune 1 (270 mg, 1.19 mmol) was dissolved in THF (6 mL) and treated with a 1.5 M solution of phenyllithium in 7:3 cyclohexane/Et$_2$O (3.2 mL, 4.76 mmol) according to the procedure outlined in example 1. The crude product was purified by flash column chromatography eluting with MeOH (containing 0.5% NH$_4$OH) in CH$_2$Cl$_2$ (0 to 10% gradient) yielding 218 mg (54%) of Example 3.

LC/MS ESI R$_T$ 1.58 min MH$^+$ 338.4

Example 4

2-[(7-Exo)-9-methyl-3-oxa-9-azabicyclo[3.3.1]non-7-yl]-1,1-di-2-thienylethanol

A solution of 6 (31 mg, 0.136 mmol) was added dropwise as a solution in THF (1 mL) with stirring to a 1 M solution of 2-thienyllithium in THF (0.54 mL, 0.54 mmol) at −30° C. (bath temp) under argon. The reaction was stirred at room temperature for 5 h, whereupon H$_2$O (2 mL) was added. The layers were separated, and the aqueous layer was extracted with EtOAc (3×1 mL). The combined organic layers were washed with saturated NaCl (1×1 mL), dried (Na$_2$SO$_4$), and concentrated under reduced pressure. The crude product was purified by flash chromatography on silica gel (8.5 g) eluting with 5% MeOH/CH$_2$Cl$_2$ (200 mL), followed by 7% MeOH/CH$_2$Cl$_2$ (100 mL), and then 10% MeOH/CH$_2$Cl$_2$ (100 mL) to give 37 mg (78%) of Example 4.

LC/MS ESI R$_T$ 1.46 min MH$^+$ 350.0

Example 5

(7-Endo)-7-(2-hydroxy-2,2-di-2-thienylethyl)-9,9-dimethyl-3-oxa-9-azoniabicyclo[3.3.1]nonane iodide A solution of Example 1 (43 mg, 0.123 mmol) and MeI (0.15 mL, 2.46 mmol) in a 2:1 mixture of CH$_2$Cl$_2$/CH$_3$CN (1.5 mL) was stirred at room temperature for 1 hour. The reaction was concentrated under reduced pressure, and the residue was triturated with Et$_2$O (2×2 mL). The washings were filtered, and the combined solid residue was dried under high vacuum to give 31 mg (52%) of Example 5.

LC/MS ESI R$_T$ 1.70 min MH$^+$ 373.0

Example 6

(7-Endo)-7-(2-cyano-2,2-di-2-thienylethyl)-9,9-dimethyl-3-oxa-9-azoniabicyclo[3.3.1]nonane bromide A 2 M solution of MeBr in tert-butyl methyl ether (1.37 mL, 2.73 mmol) was added to a solution of Example 2 (49 mg, 0.137 mmol) in acetone (1 mL). The reaction was stirred at room temperature for 4.5 d. The reaction was concentrated under reduced pressure, and the residue was triturated with Et$_2$O (4×1 mL). The washings were filtered, and the combined solid residue was dried under high vacuum to give 45 mg (72%) of Example 6.

LC/MS ESI R$_T$ 1.57 min MH$^+$ 362.4

Example 7

(7-Endo)-7-(2-cyano-2,2-diphenylethyl)-9,9-dimethyl-3-oxa-9-azoniabicyclo[3.3.1]nonane iodide Following the general procedure described in Example 2, Example 3 (112 mg, 0.33 mmol) was treated with AlCl$_3$ (218 mg, 1.64 mmol) and TMSCN (0.21 mL, 1.64 mmol) in CH$_2$Cl$_2$ (6.6 mL) in a sealed vial at 85° C. for 20 h. After cooling to room temperature, an additional 1.64 mmol of AlCl$_3$ and TMSCN was added to the reaction which was then stirred at 85° C. for another 20 h. The reaction work-up was conducted as previously described and the reaction product (69 mg, 0.20 mmol) was dissolved in 1:1 dichloromethane/acetonitrile (2 mL). MeI (0.062 mL, 1.00 mmol) and Na$_2$CO$_3$ (42 mg, 0.40 mmol) were added and the reaction mixture was stirred at room temperature for 14 h. Following filtration, the mixture was concentrated under reduced pressure and the crude product was crystallized from CH$_2$Cl$_2$/EtOAc to give 27 mg (17%) of Example 7.

LC/MS ESI R$_T$ 1.79 min MH$^+$ 361.4

Example 8

(7-Exo)-7-(2-hydroxy-2,2-di-2-thienylethyl)-9,9-dimethyl-3-oxa-9-azoniabicyclo[3.3.1]nonane bromide A 2 M solution of MeBr in tert-butyl methyl ether (0.53 mL, 1.06 mmol) was added to a solution of Example 4 (37 mg, 0.106 mmol) in acetone (2 mL). The reaction was stirred at room temperature for 17 h. The reaction was concentrated under reduced pressure, and the residue was triturated with Et$_2$O (2×5 mL). The washings were filtered, and the combined solid residue was dried under high vacuum to give 38 mg (81%) of Example 8.

LC/MS ESI R$_T$ 1.57 min MH$^+$ 364

Abbreviations

AlCl$_3$ Aluminum trichloride
CH$_2$Cl$_2$ Dichloromethane
CDCl$_3$ Deuterio chloroform
CHCl$_3$ Chloroform
CH$_3$CN Acetonitrile
ESI Electrospray ionization Et$_2$O Diethyl ether
EtOAc Ethyl acetate
HCl Hydrochloric acid
HPLC High pressure liquid chromatography
K$_2$CO$_3$ Potassium carbonate
MeBr Methyl bromide
MgSO$_4$ Magnesium sulfate
MeI Methyl iodide
MeOH Methanol
NaCl Sodium chloride
NaH Sodium hydride
NaOH Sodium hydroxide
Na$_2$SO$_4$ Sodium sulfate
NH$_4$OH Ammonium hydroxide
TFA Trifluoroacetic acid
THF Tetrahydrofuran
TLC Thin layer chromatography
TMSCN Trimethylsilyl cyanide

BIOLOGICAL EXAMPLES

The inhibitory effects of compounds at the M$_3$ mAChR of the present invention are determined by the following in vitro and in vivo functional assays:

Analysis of Inhibition of Receptor Activation by Calcium Mobilization

Stimulation of mAChRs expressed on CHO cells were analyzed by monitoring receptor-activated calcium mobilization as previously described (H. M. Sarau et al, 1999. *Mol. Pharmacol.* 56, 657-663). CHO cells stably expressing M$_3$ mAChRs were plated in 96 well black wall/clear bottom plates. After 18 to 24 hours, media was aspirated and replaced with 100 µl of load media (EMEM with Earl's salts, 0.1% RIA-grade BSA (Sigma, St. Louis Mo.), and 4 µM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 µl of assay buffer (0.1% gelatin (Sigma), 120 mM NaCl, 4.6 mM KCl, 1 mM KH$_2$ PO$_4$, 25 mM NaH CO$_3$, 1.0 mM CaCl$_2$, 1.1 mM MgCl$_2$, 11 mM glucose, 20 mM HEPES (pH 7.4)). 50 µl of compound (1×10$^{-11}$-1×10$^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 µl of acetylcholine (0.1-10 nM final), prepared in buffer containing 0.1% BSA, at a rate of 50 µl/sec. Calcium mobilization, monitored as change in cytosolic calcium concentration, was measured as change in 566 nm emission intensity. The change in emission intensity is directly related to cytosolic calcium levels. The emitted fluorescence from all 96 wells is measured simultaneously using a cooled CCD camera. Data points are collected every second. This data was then plotting and analyzed using GraphPad PRISM software.

Muscarinic Receptor Radioligand Binding Assays

Radioligand binding studies using 0.5 nM [$^3$H]-N-methyl scopolamine (NMS) in a SPA format is used to assess binding of muscarinic antagonists to M$_1$, M$_2$, M$_3$, M$_4$ and M$_5$ muscarinic acetylcholine receptors. In a 96-well plate, the SPA beads are pre-incubated with receptor-containing membrane for 30 min at 4° C. Then 50 mM HEPES and the test compound are added and incubated at room temperature (shaking) for 2 hours. The beads are then spun down and counted using a scintillation counter.

Evaluation of Potency and Duration of Action in Isolated Guinea Pig Trachea

Tracheae were removed from adult male Hartely guinea pigs (Charles River, Raleigh, N.C.; 400-600 grams) and placed into modified Krebs-Henseleit solution. Composition of the solution was (mM): NaCl 113.0, KCl 4.8, CaCl$_2$ 2.5, KH$_2$PO$_4$ 1.2, MgSO$_4$ 1.2, NaHCO$_3$ 25.0 and dextrose 11.0 which was gassed with 95% O$_2$: 5% CO$_2$ and maintained at 37° C. Each trachea was cleaned of adherent tissue and opened lengthwise. Epithelium was removed by gently rubbing the luminal surface with a cotton-tipped applicator. Individual strips were cut, approximately 2 cartilage rings in width, and suspended via silk suture in 10-ml water-jacketed organ baths containing Krebs-Henseleit solution and connected to Grass FT03C force-displacement transducers. Mechanical responses were recorded isometrically by MP100WS/Acknowledge data acquisition system (BIOPAC Systems, Goleta, Calif., www.biopac.com) run on Apple G4 computers. The tissues were equilibrated under a resting tension of 1.5 g, determined to be optimal by length-tension evaluation, and washed with Krebs-Henseleit solution every 15 minutes for one hour. After the equilibration period pulmonary tissues were contracted with 10 uM carbachol until reaching plateau, which served as a reference contraction for data analysis. Tissues were then rinsed every 15 minutes over 1 hour until reaching baseline tone. The preparations were then left for at least 30 minutes before the start of the experiment.

Concentration-response curves were obtained by a cumulative addition of carbachol in half-log increments (Van Rossum, 1963, Arch. Int. Pharmacodyn., 143:299), initiated at 1 nM. Each concentration was left in contact with the preparation until the response plateaued before the addition of the subsequent carbachol concentration. Paired tissues were exposed to mAChR antagonist compounds or vehicle for 30 min before carbachol cumulative concentration-response curves were generated. All data is given as mean ±standard error of the mean (s.e.m.) with n being the number of different animals.

For superfusion (duration of action) studies, the tissues were continuously superfused with Krebs-Henseleit solution at 2 ml/min for the duration of the experiment. Stock solutions of agonist and antagonist were infused (0.02 ml/min) via 22-guage needle inserted into the superfusion tubing. Mechanical responses were recorded isometrically using a commercially-available data acquisition system (MP100WS/Acknowledge; BIOPAC Systems, Goleta, Calif., www.biopac.com) interfaced with a Macintosh G4 computer (Apple, Cupertino, Calif. www.apple.com). The tissues were suspended under an optimal resting tension of 1.5 g. After a 60 min equilibration period, the tissues were contracted with carbachol (1 uM) for the duration of the experiment. Upon reaching a sustained contraction isoproterenol (10 uM) was administered to maximally relax the tissue, and this change served as a reference. Isoproterenol exposure was halted and the carbachol-induced tension allowed to recover. Muscarinic receptor antagonists infused at a single concentration per tissue until a sustained level of inhibition was attained. The compound was then removed and, once again, the carbachol-induced tension was allowed to recover.

The following parameters were determined for each concentration of antagonist, and expressed as the mean±S.E.M. for n individual animals. Inhibition of the carbachol-induced contraction was expressed as a percent of the reference response (isoproterenol) and the time required to reach one-half of this relaxation was measured (onset of response). The tension recovery following removal of the compound was determined as was the time required to reach one-half of the maximum tension recovery (offset of response). At 60 and 180 minutes after removal of the antagonist the remaining level of inhibition was determined and expressed as a percent of the isoproterenol reference.

Antagonist concentration-response curves were obtained by plotting the maximal relaxation data at 0, 60 and 180-min following antagonist withdrawal. Recovery, termed shift, was calculated from the ratio of the 0-min inhibition curve $IC_{50}$ and the concentration of compound yielding a similar tension recovery at 60 and 180 minutes.

Halftimes for onset and offset of response were plotted vs. corresponding concentration and the data were fit with non-linear regression. These values were extrapolated at the $IC_{50}$ (determined from the inhibition concentration-response curve) and designated $Ot_{50}$ (time required, at the $IC_{50}$ concentration, to reach half of the onset response) and $Rt50$ (time required, at the $IC_{50}$ concentration, to reach half of the recovery response).

Methacholine-Induced Bronchoconstriction—Potency and Duration of Action

Airway responsiveness to methacholine was determined in awake, unrestrained Balb C mice (n=6 each group). Barometric plethysmography was used to measure enhanced pause (Penh), a unitless measure that has been shown to correlate with the changes in airway resistance that occur during bronchial challenge with methacholine(2). Mice were pre-treated with 50 µl of compound (0.003-10 µg/mouse) in 50 µl of vehicle (10% DMSO) intranasally (i.n.) and were then placed in the plethysmography chamber a given amount of time following drug administration (15 min—96 h). For potency determination, a dose response to a given drug was performed, and all measurements were taken 15 min following i.n. drug administration. For duration of action determination, measurements were taken anywhere from 15 min to 96 hours following i.n. drug administration.

Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software. This experiment allows the determination of duration of activity of the administered compound.

The present compounds are useful for treating a variety of indications, including but not limited to respiratory-tract disorders such as chronic obstructive lung disease, chronic bronchitis, asthma, chronic respiratory obstruction, pulmonary fibrosis, pulmonary emphysema, and allergic rhinitis.

Formulation-Administration

Accordingly, the present invention further provides a pharmaceutical formulation comprising a compound of formula (I), or a pharmaceutically acceptable salt, solvate, or physiologically functional derivative (e.g., salts and esters) thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

Compounds of formula (I) will be administered via inhalation via the mouth or nose.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di- or poly-saccharides (e.g., lactose or starch), organic or inorganic salts (e.g., calcium chloride, calcium phosphate or sodium chloride), polyalcohols (e.g., mannitol), or mixtures thereof, alternatively with one or more additional materials, such additives included in the blend formulation to improve chemical and/or physical stability or performance of the formulation, as discussed below, or mixtures thereof. Use of lactose is preferred. Each capsule or cartridge may generally contain between 20 µg-10 mg of the compound of formula (I) optionally in combination with another therapeutically active ingredient. Alternatively, the compound of the invention may be presented without excipients, or may be formed into particles comprising the compound, optionally other therapeutically active materials, and excipient materials, such as by co-precipitation or coating.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant as an inhaler having a reservoir form pack suitable for comprising multiple (un-metered doses) of medicament in dry powder form and including means for metering medicament dose from the reservoir to a delivery position. The metering means may for example comprise a metering cup or perforated plate, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disk-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum aerodynamic particle size for inhalation into the bronchial system for localized delivery to the lung is usually 1-10 µm, preferably 2-5 µm. The optimum aerodynamic particle size for inhalation into the alveolar region for achieving systemic delivery to the lung is approximately 0.5-3 µm, preferably 1-3 µm. Particles having an aerodynamic size above 20 µm are generally too large when inhaled to reach the small airways. Average aerodynamic particle size of a formulation may measure by, for example cascade impaction. Average geometric particle size may be measured, for example by laser diffraction, optical means.

To achieve a desired particle size, the particles of the active ingredient as produced may be size reduced by conventional means e.g. by controlled crystallization, micronisation or nanomilling. The desired fraction may be separated out by air classification. Alternatively, particles of the desired size may be directly produced, for example by spray drying, controlling the spray drying parameters to generate particles of the desired size range. Preferably, the particles will be crystalline, although amorphous material may also be employed where desirable. When an excipient such as lactose is employed, generally, the particle size of the excipient will be much greater than the inhaled medicament within the present invention, such that the "coarse" carrier is non-respirable. When the excipient is lactose it will typically be present as milled lactose, wherein not more than 85% of lactose particles will have a MMD of 60-90 µm and not less than 15% will have a MMD of less than 15 µm. Additive materials in a dry powder blend in addition to the carrier may be either respirable, i.e., aerodynamically less than 10 microns, or non-respirable, i.e., aerodynamically greater than 10 microns.

Suitable additive materials which may be employed include amino acids, such as leucine; water soluble or water insoluble, natural or synthetic surfactants, such as lecithin (e.g., soya lecithin) and solid state fatty acids (e.g., lauric, palmitic, and stearic acids) and derivatives thereof (such as salts and esters); phosphatidylcholines; sugar esters. Additive materials may also include colorants, taste masking agents (e.g., saccharine), anti-static-agents, lubricants (see, for example, Published PCT Patent Appl. No. WO 87/905213, the teachings of which are incorporated by reference herein), chemical stabilizers, buffers, preservatives, absorption enhancers, and other materials known to those of ordinary skill.

Sustained release coating materials (e.g., stearic acid or polymers, e.g. polyvinyl pyrolidone, polylactic acid) may also be employed on active material or active material containing particles (see, for example, patent Nos. U.S. Pat. No. 3,634,582, GB 1,230,087, GB 1,381,872, the teachings of which are incorporated by reference herein).

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as herein before recited, or an appropriate fraction thereof, of the active ingredient.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follow

What is claimed is:

1. A compound of formula (I) as indicated below:

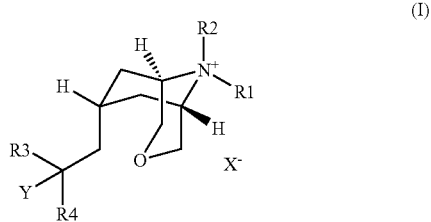

(I)

wherein

R1 and R2 are, independently, selected from the group consisting of a bond, hydrogen, $(C_1-C_{12})$alkyl, $(C_2-C_{10})$alkenyl, $(C_1-C_6)$alkyl$(C_3-C_6)$cycloalkyl, $(C_1-C_{10})$alkyl-aryl, $(C_1-C_{10})$alkyl-OH, $(C_1-C_6)$ alkyl-CN, $(C_1-C_{10})$alkyl-halogen, $(C_1-C_6)$alkyl-$CF_3$, $(C_1-C_6)$alkyl-alkoxy, and $(C_1-C_6)$alkyl-O—$(C_1-C_6)$alkyl-$OCH_3$;

R3 and R4 are, independently, selected from the group consisting of straight or branched chain lower alkyl having from 1 to 6 carbon atoms, cycloalkyl having from 5 to 6 carbon atoms, cycloalkyl-alkyl having 6 to 10 carbon atoms, 2-thienyl, aryl, aryl, heteroaryl having 5 to 6 carbon atoms and N or O as the heteroatom, heteroaryl having 5 to 6 carbon atoms and N or O as the heteroatom, heterocycloalkyl having 5 to 6 carbon atoms and N or O as the heteroatom, and heterocycloalkyl-alkyl having 6 to 10 carbon atoms and N or O as the heteroatom;

Y is hydroxy or cyano; and $X^-$ is a physiologically acceptable anion associated with the positive charge of the N atom.

2. A pharmaceutical composition comprising a compound according to claim 1 and a pharmaceutically acceptable carrier thereof.

3. The compound according to claim 1 wherein $X^-$ is chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

4. The compound according to claim 1 wherein R3 and R4 are thienyl.

5. The compound according to claim 1 wherein R3 and R4 are aryl.

6. The compound according to claim 5 wherein R3 and R4 are phenyl.

7. The compound according to claim 1 wherein Y is hydroxyl.

8. The compound according to claim 1 wherein Y is cyano.

9. The compound according to claim 4 wherein Y is hydroxyl.

10. The compound according to claim 4 wherein Y is cyano.

11. The compound according to claim 6 wherein Y is hydroxyl.

12. The compound according to claim 6 wherein Y is cyano.

13. The compound according to claim 1 wherein R1 and R2 are both methyl.

14. The compound according to claim 13 wherein R3 and R4 are phenyl, or thienyl.

15. The compound according to claim 14 wherein Y is hydroxyl.

16. The compound according to claim 14 wherein Y is cyano.

17. The compound according to claim 1 wherein one of R1 and R2 are a bond and the other is methyl.

18. The compound according to claim 17 wherein R3 and R4 are phenyl or thienyl.

19. The compound according to claim 18 wherein Y is hydroxyl.

20. The compound according to claim 18 wherein Y is cyano.

21. The compound according to claim 1 which is:
2-[(3-Endo)-9-methyl-3-oxa-9-azabicyclo[3.3.1]non-7-yl]-1,1-diphenylethanol;
2-[(7-Endo)-9-methyl-3-oxa-9-azabicyclo[3.3.1]non-7-yl]-1, 1-di-2-thienylethanol;
(7-Endo)-7-(2-hydroxy-2,2-di-2-thienylethyl)-9, 9-dimethyl-3-oxa-9-azoniabicyclo [3.3.1]nonane iodide;
(7-Endo)-7-(2-cyano-2,2-di-2-thienylethyl)-9, 9-dimethyl-3-oxa-9-azoniabicyclo [3.3.1]nonane bromide;
(7-Endo)-7-(2-cyano-2,2-diphenylethyl)-9, 9-dimethyl-3-oxa-9-azoniabicyclo [3.3.1]nonane iodide; or
(7-Exo)-7-(2-hydroxy-2,2-di-2-thienylethyl)-9, 9-dimethyl-3-oxa-9-azoniabicyclo [3.3.1]nonane bromide.

* * * * *